(12) United States Patent
Thoms

(10) Patent No.: US 7,010,223 B2
(45) Date of Patent: Mar. 7, 2006

(54) DENTAL OR ENDOSCOPIC CAMERA

(75) Inventor: Michael Thoms, Bietigheim-Bissingen (DE)

(73) Assignee: Dürr Dental GmbH & Co. KG, Bietigheim-Bissingen (DE)

( * ) Notice: Subject to any disclaimer, the term of this patent is extended or adjusted under 35 U.S.C. 154(b) by 0 days.

(21) Appl. No.: 10/478,774

(22) PCT Filed: Apr. 29, 2002

(86) PCT No.: PCT/EP02/04699

§ 371 (c)(1),
(2), (4) Date: Nov. 21, 2003

(87) PCT Pub. No.: WO02/096277

PCT Pub. Date: Dec. 5, 2002

(65) Prior Publication Data

US 2004/0156626 A1     Aug. 12, 2004

(30) Foreign Application Priority Data

May 26, 2001   (DE) ............................... 101 25 772

(51) Int. Cl.
*A61B 1/04*   (2006.01)
*G03B 29/00*  (2006.01)

(52) U.S. Cl. ......................................... 396/16; 348/66
(58) Field of Classification Search ................. 348/65, 348/66; 359/738, 798, 809; 396/16, 17
See application file for complete search history.

(56) References Cited

U.S. PATENT DOCUMENTS

| 4,969,450 | A |   | 11/1990 | Chinnock et al. |
| 5,416,638 | A |   | 5/1995  | Broome |
| 5,598,205 | A | * | 1/1997  | Nishioka ............ 348/65 |
| 6,002,424 | A | * | 12/1999 | Rapa et al. .......... 348/66 |
| 6,117,071 | A |   | 9/2000  | Ito et al. |

FOREIGN PATENT DOCUMENTS

| DE | 4102614 C2  | 1/1991 |
| DE | 19924351 A1 | 5/1999 |
| WO | WO 94/09694 | 10/1993 |
| WO | WO 99/06871 | 7/1998 |

* cited by examiner

*Primary Examiner*—Christopher Mahoney
(74) *Attorney, Agent, or Firm*—Watson IP Group, PLC; Jovan N. Jovanovic

(57) ABSTRACT

According to the invention, the lens system of a dental or endoscopic camera is designed in the form of a non-telecentric lens in which the field stop or an image thereof is located in the region of the lens arrangement on the converter side of said lens system.

13 Claims, 3 Drawing Sheets

DENTAL OR ENDOSCOPIC CAMERA

BACKGROUND OF THE INVENTION

1. Field of the Invention

The invention relates to a dental or endoscopic camera, and more particularly, to a dental or endoscopic camera having a casing, with an optical system, with a stop determining the image field and with an image converter arranged on the axis of the optical system, wherein the optical system has an object-side lens arrangement, a middle lens arrangement and a converter-side lens arrangement.

2. Background Art

In cameras of such a type the optical system is constructed in the form of a telecentric optical system, as is generally the case in cameras. In order to guarantee good image-forming properties with such an optical system, the object-side lens arrangement, the middle lens arrangement and the converter-side lens arrangement have to be constructed from several (as a rule, two) individual lenses. For this reason, the optical systems for cameras of such a type are expensive.

By virtue of the present invention, a camera a casing, with an optical system, with a stop determining the image field and with an image converter arranged on the axis of the optical system, wherein the optical system has an object-side lens arrangement, a middle lens arrangement and a converter-side lens arrangement is intended to be developed further in such a way that it can be produced more inexpensively while still having good image-forming properties.

SUMMARY OF THE INVENTION

In accordance with the invention, this object is achieved by virtue of a camera having the stop determining the field of view, or an image of the same, is situated in the region of the converter-side lens arrangement.

Surprisingly, it has been found that a good overall image with such a camera is obtained even when the principle of the telecentric beam path, which is tried and tested as such in cameras, is departed from. With a non-telecentric beam path, in dental and endoscopic cameras use may also be made of lens arrangements that, in themselves, do not have particularly good image-forming properties. In particular, the individual lens arrangements may also be realised by individual lenses. A considerable cost-saving is obtained by this means, since fewer lenses are required and the assembly of the optical system is also simplified.

In a preferred embodiment, the stop determining the field of view, or its image, is situated a short distance downstream of the converter-side lens arrangement amounting to approximately 2% to 10%, preferably approximately 2% to approximately 5%, of the spacing between the rear boundary face of the converter-side lens arrangement and the light-sensitive face of the image converter. If the field stop is set in such a way, particularly good image-forming properties arise. The third lens arrangement is used in its middle region, where the distortion errors are slight. The middle lens arrangement is also used in its marginal regions. But it does not need to have any greatly curved surfaces, so the use of the marginal regions of this lens arrangement also does not result in unacceptable distortion errors.

In a preferred embodiment, the object-side lens arrangement is formed by a concavely/convexly curved lens. Accordingly, the first lens arrangement may be constructed from only one optical component which has very simple geometry.

In another preferred embodiment, the middle lens arrangement is formed by a biconvex lens, and the converter-side lens arrangement may also be formed by a biconvex lens. Such embodiments provide particularly simple possibilities for realising the middle lens arrangement and the converter-side lens arrangement, respectively.

In another preferred embodiment, a light-reflecting means is arranged upstream of the object-side lens arrangement. Such an embodiment is particularly well suited to be used for dental purposes, since the direction of view is inclined in relation to the axis of the handpiece, in particular is perpendicular to said axis.

In another preferred embodiment, an entrance window situated upstream of the object-side lens arrangement is connected to the casing in a flush and tight manner. Such an embodiment is advantageous with regard to simple cleaning and sterilising of the camera.

In a preferred embodiment, the camera further includes a device for adjusting the image converter in the direction of the axis of the optical system. Such a camera can be used both for viewing an object from the immediate vicinity and for viewing an object from a greater distance. In the case of a dental camera, the dentist may, for example, record details of one tooth or an overall view of the dentition.

In one such embodiment, the adjusting device includes an actuating element which passes through a wall of the casing. Such an embodiment affords a particularly simple possibility for adjusting the focusing distance.

In another such preferred embodiment, the adjusting device has an electric motor which is exited via a plug-and-socket connection via which the image converter is also connected to an image-evaluation circuit. In the case of such a camera, adjustment of the focusing distance is possible without a moving part having to be passed through the wall of the casing of the camera.

In another embodiment the camera further includes an optical waveguide extending within the casing, the light-output end of which is adjacent to an entrance window of the casing. In one such embodiment, the camera may include several light-sources, such as, for example, light-emitting diodes 15, arranged next to the entrance window. With such an embodiment, a good illumination of the object in front of the camera is guaranteed.

BRIEF DESCRIPTION OF THE DRAWINGS

The invention will be elucidated in more detail below on the basis of exemplary embodiments with reference to the drawing. Shown in the latter are.

DETAILED DESCRIPTION OF THE DRAWINGS

Figure 1:
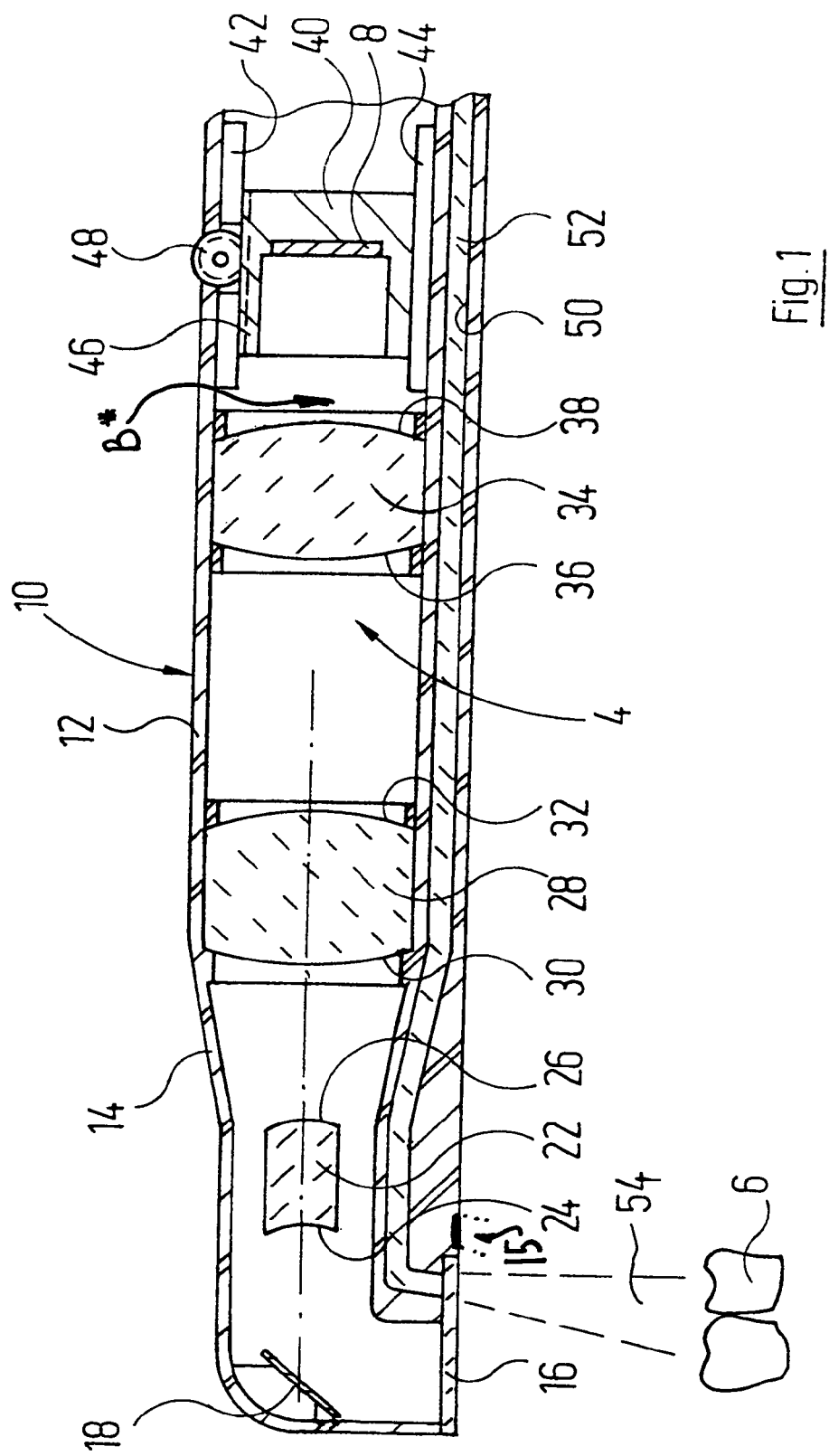
FIG. 1: an axial section through a dental camera.

While this invention is susceptible of embodiment in many different forms, there is shown in the drawings and described herein in detail a specific embodiment with the understanding that the present disclosure is to be considered as an exemplification of the principles of the invention and is not intended to limit the invention to the embodiment illustrated.

The dental camera that is reproduced in the drawing has a casing 10 which is produced in the form of a plastic injection-moulded part. The casing 10 has been reproduced in the form of a one-part casing; it goes without saying that, depending on the production requirements, a person skilled in the art may construct it in the form of a multi-part casing, the various parts of the casing then being tightly connected to one another, subject to insertion of seals, or bonded or welded to one another.

The casing 10 has a gripping section 12 which has substantially the form of a cylindrical sleeve that is closed at the ends. The gripping section 12 bears at its free end a tapering and angled casing section 14, the downward-turned end of which is sealed in flush and tight manner by means of a window 16.

In the casing 10 there is arranged an optical system, denoted overall by 4, which forms an image of a schematically indicated object 6 (a tooth or mandibular arch) onto an image converter 8. The image converter 8 may be a colour CCD.

In the angled part of the casing section 14 there is arranged a reflecting mirror 18 which is set at 45 degrees in relation to the axis of the gripping section 12 and in relation to the axis of the window 16 and may also take the form of a reflecting prism, for example a right-angled prism or pentaprism.

In the beam path downstream of the reflecting mirror 18 there is arranged a lens 22 which has a concave front end face 24 and a convex rear end face 26.

At a relatively large distance from the lens 22 there is arranged an intermediate lens 28 which has a convex object-side end face 30 and a convex converter-side end face 32.

In turn, a relatively large distance downstream of the intermediate lens 24 a converter-side lens 34 is provided which has a convex object-side end face 36 and a convex converter-side end face 38.

The image converter 8 is arranged on a slide 40 which is movably guided along the axis of the optical system 4 by guide ribs 42, 44 which are provided on the inside of the casing 10. On the one longitudinal face of the slide 40 a toothed rack 46 is formed which meshes with a toothed wheel 48 which is rotatably supported on the casing 10 and which projects, with one toothed-wheel section, outwards through the casing 10. By rotation of the toothed wheel 48, the image converter 8 can consequently be adjusted along the axis of the optical system 4.

In the casing 10 a channel 50 is provided which extends substantially in the axial direction and in which an optical waveguide 52 is provided. An end section of the channel 50 and an end section of the optical waveguide 52 are angled in such a way that light transmitted to the optical waveguide 52 leaves the optical waveguide 52 slightly inclined in relation to the axis of the window 16, as shown at 54.

Via a plug-and-socket connection which is not reproduced in the drawing (to be imagined on the right therein), the image converter 8 and the optical waveguide 52 are connected to a supply hose which has a cable leading to an image-evaluation circuit and also a further optical waveguide which leads to a cold-light source.

Figure 2:
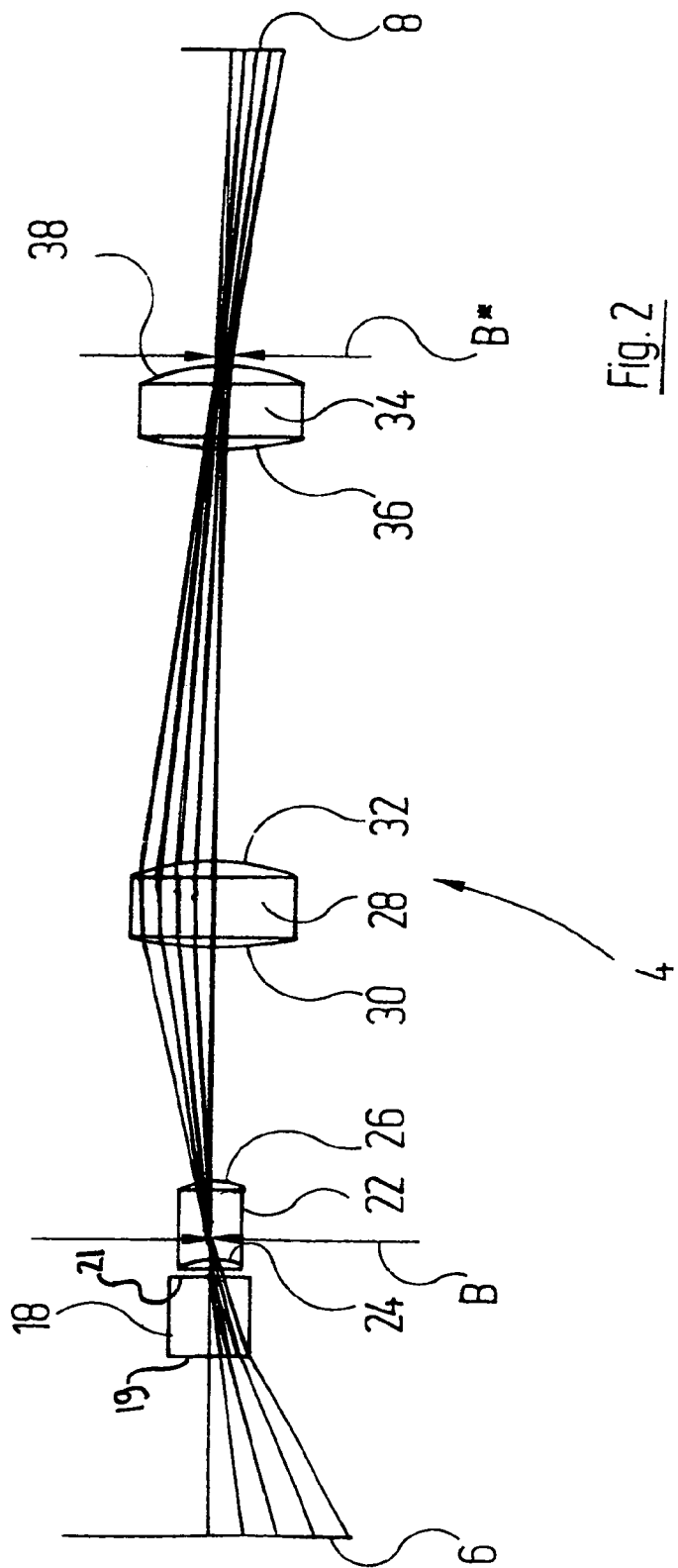
FIG. 2: a schematic view of the optical system of the dental camera according to FIG. 1.

The beam path of the optical system 4 is shown in still more precise manner in FIG. 2. For the sake of greater ease of representation, the conditions have been shown as they would obtain in the case of a direct-vision camera which is obtained from the camera according to FIG. 1 if the reflecting mirror 18 taking the form of a reflecting prism is replaced by a plane-parallel glass plate of the same optical thickness and if the window 16 is provided on the axis of the gripping section 12. The various optical components are again denoted as in FIG. 1. In addition, various beams have been drawn in which lead from different points on the object 6 to assigned points on the surface of the image converter 8.

It will be discerned that in the case of the optical system shown in FIG. 2 an image B, conjugate with the field stop B*, is disposed in the vicinity of the lens 22. It will be discerned that with such a position of the field stop B*, or of the image B of the same, the object-side lens 22 is utilised substantially in its middle region, the intermediate lens 28 is also utilised in its marginal regions and the converter-side lens 34 is again used only in its central region.

By reason of the arrangement of the three lenses which is shown, in which the intermediate lens 28 is clearly spaced both from the object-side lens 22 and from the converter-side lens 34, the intermediate lens 28 does not need to have any sharply curved surfaces. As a result, optical aberrations are reduced. The fact that the marginal regions are also utilised in the intermediate lens 28 consequently does not result in an unacceptable distortion of the image.

The following table specifies a concrete exemplary embodiment of one possible way of realising the optical system 4. The conditions correspond to the representation of FIG. 2.

In this table there are listed respectively: the number of the end face (reference symbol of FIG. 1 or 2), the radius of curvature of the corresponding end face, the thickness of the layer of material adjoining the end face, and the type of the optical medium (type of glass; A=air) which is situated downstream of the corresponding face. In the final column the diameter of the respective end face is specified. The unit of length is 1 mm in each case.

| Face | Radius | Thickness | Glass | Diameter |
|---|---|---|---|---|
| 6 | ∞ | 9 | A | 13.21 |
| 19 | ∞ | 4 | SF8 | 3.80 |
| 21 | ∞ | 0.76 | A | 1.54 |
| 24 | −2.31 | 4.00 | N-LASF30 | 3.00 |
| 26 | −2.65 | 11.83 | A | 3.00 |
| 30 | 24.30 | 4 | N-LASF30 | 7.50 |
| 32 | −11.94 | 20.84 | A | 7.50 |
| 36 | 12.15 | 4.00 | N-ZK7 | 7.50 |
| 38 | −8.82 | 0.56 | A | 7.50 |
| Stop B* | ∞ | 15.13 | A | 0.98 |
| Converter | ∞ | | | 4.85 |

Where "A" is specified in the Glass column, it is a question of air gaps. The glass-types correspond to the catalogue of optical glasses produced by Schott.

Figure 3:
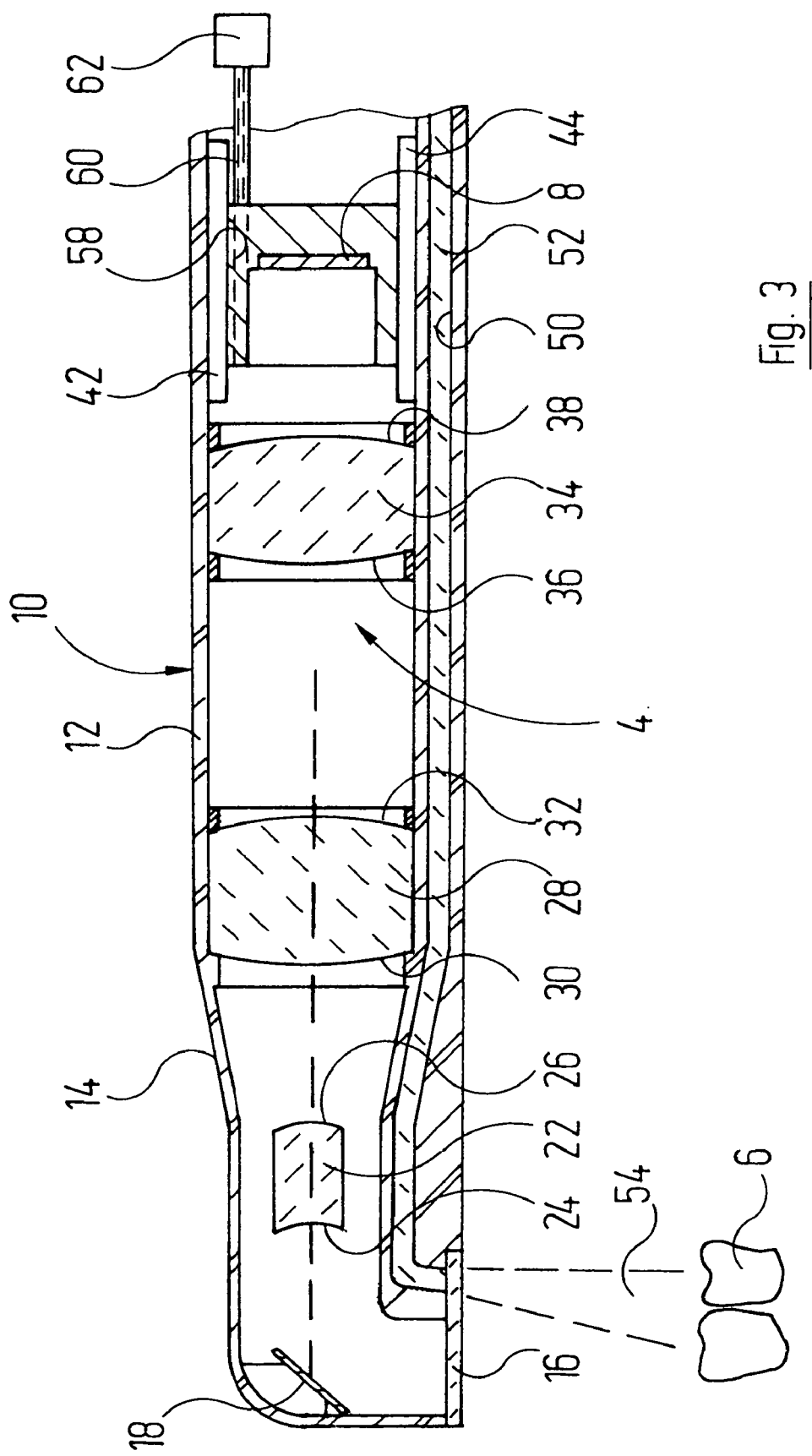
FIG. 3: a view which is similar to FIG. 1 but in which a modified adjusting mechanism for the image converter is shown.

The exemplary embodiment according to FIG. 3 largely corresponds to that according to FIG. 1; corresponding components are again provided with the same reference symbols and will not be described again in any detail.

In the case of the exemplary embodiment according to FIG. 3, the slide 40 is provided with a threaded bore 58 in which a threaded spindle 60 moves. The threaded spindle 60 is driven by an electric motor 62 which is borne by the casing 10. The supply lines for the electric motor 62 lead to a supply hose in precisely the same manner, via the plug-and-socket connection to be imagined on the right of FIG. 3, as the connecting leads of the image converter 8 and the optical waveguide 52.

In this way the converter 8 can be adjusted along the axis of the optical system 4 without a mechanical bushing having to be provided through the wall of the casing 10.

The foregoing description merely explains and illustrates the invention and the invention is not limited thereto except insofar as the appended claims are so limited, as those skilled in the art who have the disclosure before them will be able to make modifications without departing from the scope of the invention.

What is claimed is:

1. A dental or endoscopic camera comprising a casing, with an optical system, with a stop determining the image field and with an image converter arranged on the axis of the optical system, wherein the optical system has an object-side lens arrangement, a middle lens arrangement and a converter-side lens arrangement, wherein the stop determining the image field is situated in the region of the converter-side lens arrangement, a short distance downstream of the converter-side lens arrangement amounting to approximately 2% to 10%, of the spacing between a rear boundary face of the converter-side lens arrangement and a light-sensitive face of the image converter.

2. The camera according to claim 1, the short distance downstream amounts to approximately 2% to approximately 5%, of the spacing between the rear boundary face of the converter-side lens arrangement and the light-sensitive face of the image converter.

3. The camera according to claim 1, wherein the object-side lens arrangement is formed by a concavely/convexly curved lens.

4. The camera according to claim 1, wherein the middle lens arrangement is formed by a biconvex lens.

5. The camera according to claim 1, wherein the converter-side lens arrangement is formed by a biconvex lens.

6. The camera according to claim 1, further comprising a light-reflecting means arranged upstream of the object-side lens arrangement.

7. The camera according to claim 1, wherein an entrance window is situated upstream of the object-side lens arrangement and is connected to the casing in flush and tight manner.

8. The camera according to claim 1, further comprising a device for adjusting the image converter in the direction of the axis of the optical system.

9. The camera according to claim 8, wherein the adjusting device has an actuating element which passes through a wall of the casing.

10. The camera according to claim 8, wherein the adjusting device has an electric motor for adjusting the image converter in the direction of the axis of the optical system.

11. The camera according to claim 1, further comprising an optical waveguide extending within the casing, the light-output end of which is adjacent to an entrance window of the casing.

12. The camera according to claim 1, further comprising at least one light-source arranged next to the entrance window.

13. The camera according to claim 12 wherein at least one of the at least one light-source comprises a light-emitting diode.

* * * * *